United States Patent [19]

McGuire

[11] Patent Number: 5,746,757
[45] Date of Patent: May 5, 1998

[54] SUTURING JIG AND METHOD FOR USING SAME

[76] Inventor: David A. McGuire, 3418 Lakeside Dr., Anchorage, Ak. 99515

[21] Appl. No.: 784,401

[22] Filed: Jan. 17, 1997

Related U.S. Application Data

[60] Provisional application No. 60/010,101, Jan. 17, 1996.
[51] Int. Cl.$^6$ ............................................. A61B 17/04
[52] U.S. Cl. .................... 606/148; 606/139; 606/144; 606/205
[58] Field of Search ..................... 606/148, 139, 606/144, 145, 205, 206, 207, 210

[56] References Cited

U.S. PATENT DOCUMENTS 5,188,636  2/1993  Fedotov ............................ 606/144
5,411,481  5/1995  Allen et al. ....................... 606/144

FOREIGN PATENT DOCUMENTS 378427  10/1907  France ............................ 606/144

*Primary Examiner*—Michael Buiz
*Assistant Examiner*—Tina T. D. Pham
*Attorney, Agent, or Firm*—Bromberg & Sunstein LLP

[57] ABSTRACT

A suturing jig for attaching strands of tissue for use as a ligament replacement in cruciate ligament reconstruction. The suturing jig is provided with two pivotally attached arms having at their respective distal ends a clamping member. Each clamping member includes a plurality of openings. Each opening on one clamping member is aligned with a corresponding opening on the other clamping member for providing a path through which a needle may pass.

36 Claims, 3 Drawing Sheets

5,746,757

SUTURING JIG AND METHOD FOR USING SAME

CROSS REFERENCE

This application claims priority from provisional application serial number 60/010,101, filed Jan. 17, 1996, which is hereby incorporated herein by reference.

TECHNICAL FIELD

This invention generally relates to devices for use in cruciate ligament surgery, and in particular, for suturing connective tissues for ligament replacement grafts.

BACKGROUND ART

Typically, when performing cruciate ligament reconstruction, a bone tunnel is formed in the tibia and in the femur so that a ligament replacement graft may be inserted and secured therein. A ligament replacement graft may be a semitendinosus tendon, a patellar tendon, or other ligament replacement attached to and between a pair of bone blocks which have been sized for close fitting arrangement within one of the femoral and tibial tunnels.

The ligament replacement that is attached to and between the bone blocks may be a loop formed from at least two independent strands of tissue that have been connected to one another at their respective ends. More often than not, however, as the strands of tissue tend to be relatively narrow and slippery, the alignment and security of their respective ends for suturing purposes are rather difficult.

Suturing devices, such as that disclosed in U.S. Pat. No. 4,493,323 (Albright et al.) for suturing torn meniscus or cartilage within a patient, are effective only when used against relatively immobile meniscus or cartilage. In particular, the Albright device is designed to push one portion of the torn cartilage against a second relatively immobile portion of the cartilage during suturing. The formation of a ligament replacement loop for cruciate ligament reconstruction, on the other hand, is performed outside the patient with individual strands of tissue that are not anchored by the patient's body. Consequently, if a device such as that disclosed in Albright et al. is used for suturing the respective ends of each strand to form a ligament replacement loop, the ends would simply move away from the device or else not remain in alignment.

It is therefore desirable to provide a device that can be used to secure the adjacent strands of ligament replacement and at the same time maintain an alignment between the strands of ligament replacement for suturing.

SUMMARY OF THE INVENTION

The suturing jig that is the subject of the present invention includes a pair of opposing clamping members, each having a plurality of openings and a plurality of slots. The suturing jig also includes a first arm being attached at its distal end to one clamping member, and a second arm being attached at its distal end to the other clamping member. In general, the arms are pivotally connected to one another so as to variably adjust a distance between the clamping members. In one embodiment of the invention, the openings on each clamping member are arranged in parallel rows such that each opening on one clamping member is aligned with a corresponding opening on the other clamping member. Additionally, each of the slots is positioned between certain adjacent openings so that a portion of a suture thread may move between these adjacent openings. Specifically, each slot allows the suture thread to avoid interference with the clamping member when the suture thread has been maneuvered to loop around the strands of tissue.

In use, the strands of tissue are initially secured between the clamping members. A needle with an attached suture thread may then be inserted through an opening on one clamping member, pushed across the strands of tissues, and pulled out through a correspondingly aligned opening on the opposing clamping member. Subsequently, the needle may be inserted into an adjacent opening, and pushed across the strands of tissue. As the needle is being pulled through a correspondingly aligned opening, the suture thread is advanced across the slot between the adjacent openings until the suture thread is pulled against the strands of tissue.

DESCRIPTION OF SPECIFIC EMBODIMENTS

Figure 1:
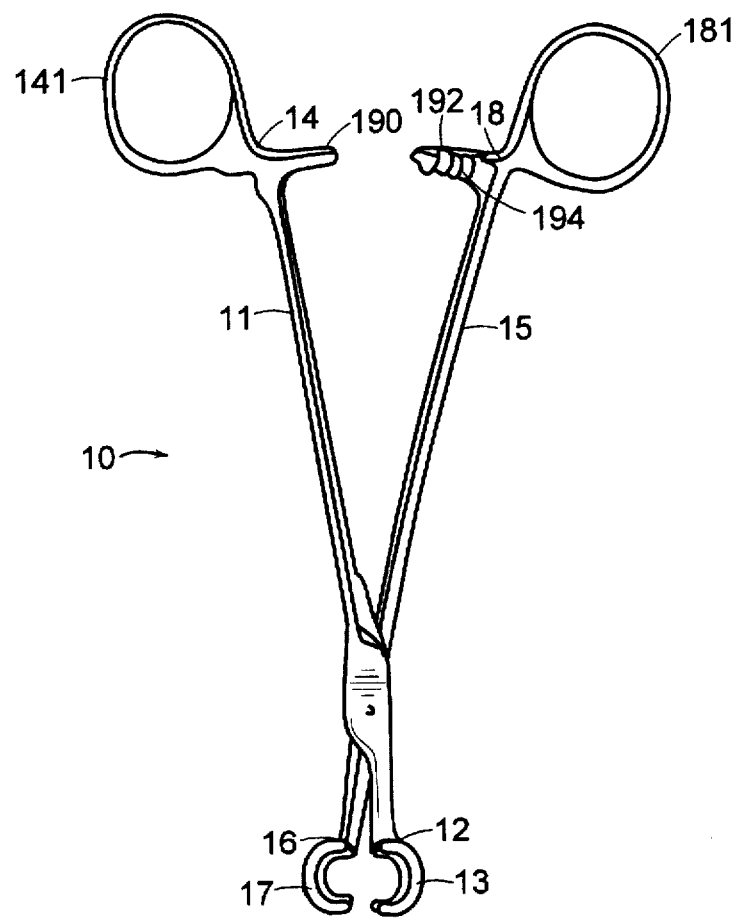
FIG. 1 is a perspective view of a suturing jig in accordance with one embodiment of the present invention.

Referring now to FIG. 1, a suturing jig 10, having a first arm 11 and a second arm 15 of substantially equal length, is designed for use in suturing strands of tissue, for example, semitendinosus tendons or patellar tendons, so that the strands of tissue may be used as a ligament replacement in cruciate ligament reconstruction.

The first arm 11, made from a rigid material, is provided at its distal end 12 with a first clamping member 13. The second arm 15, also made of a rigid material, is similarly provided at its distal end 16 with a second clamping member 17. The clamping members 13 and 17 are designed to secure strands of tissue therebetween. In one embodiment of the present invention, arms 11 and 15 are pivotally attached to one another, and may be adjusted in a manner associated with the operation of a pair of pliers. The pivotal attachment permits the arms 11 and 15 to vary a distance between the first clamping member 13 and the second clamping member 17 so as to accommodate strands of tissue having a variety of combined width. It should be noted that although the pivotal attachment between the first arm 11 and the second arm 15 may be at any corresponding point along their respective length, arms 11 and 15 are preferably attached at a point near their respective clamping members 13 and 17. In this manner, arms 11 and 15 may be adjusted to tightly secure and thereby maintain the alignment of the strands of tissue between clamping members 13 and 17 for suturing.

Figure 2:
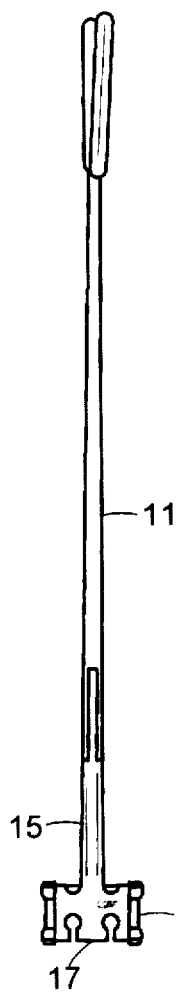
FIG. 2 illustrates the suturing jig shown in FIG. 1, rotated about its longitudinal axis by 90 degrees.

The first and second clamping members 13 and 17, being respectively attached to arms 11 and 15, are oriented toward one another so that when they are engaged, the clamping members 13 and 17 may form a continuous structure to securely hold the strands of tissue therein. For additional security when maintaining a hold on the strands of tissue, the first and second clamping members 13 and 17, when view from the perspective of FIG. 2, are sized so that they are substantially wider than the arms 11 and 15. Furthermore, in accordance with a presently preferred embodiment of the invention, the width of the first clamping member 13 is slightly wider than the width of the second clamping member 17. By providing the first clamping member 13 with a slightly wider width, the second clamping member 17 may be partially received within the first clamping member to ensure a close and secure fit.

Figure 3:
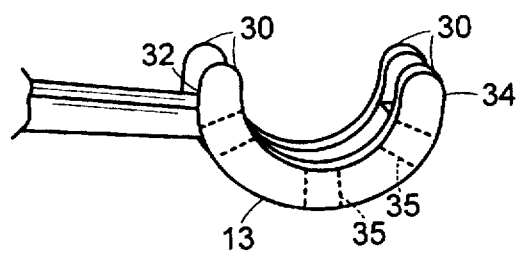
FIG. 3 shows a side view of a clamping member of the suturing jig shown in FIG. 1.
Figure 4:
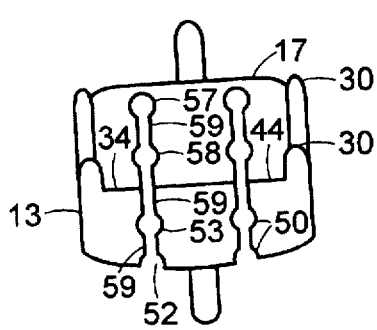
FIG. 4 shows a front end view of the clamping member shown in FIG. 3 engaging a second clamping member.

To receive the second clamping member 17, the first clamping member 13, as illustrated in FIG. 3, is equipped with a pair of substantially parallel extensions 30 at its proximal edge 32 and distal edge 34. Each pair of parallel extensions 30 are sufficiently spaced apart so that when the second clamping member 17 is brought into a close fitting engagement with the first clamping member 13, the proximal and distal edges of the second clamping member 17 may correspondingly engage the proximal and distal edges of the first clamping member 13 between the parallel extensions 30 (FIG. 4). It should be appreciated that although clamping members 13 and 17 are illustrated as arcuate in shape, they may nevertheless be made to have any shape so long as the shape is sufficient to allow the strands of tissue to be securely held between the clamping members.

Figure 5:
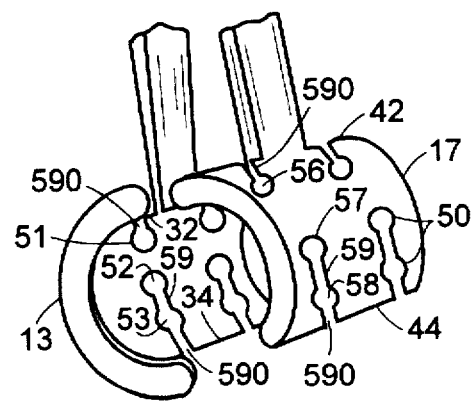
FIG. 5 illustrates the clamping members shown in FIG. 4 disengaged from one another.

Looking now at FIG. 5, clamping members 13 and 17 are shown to have a plurality of openings 50. These openings are necessary as they allow the strands of tissue to be attached to one another at more than one point. Generally, strands of tissue that are connected to one another at more than one point tend to have a relatively stronger bond than strands that do not. The openings 50, as can be seen in FIG. 5, are in alignment with respect to one another. In a preferred embodiment of the present invention, the openings 50 on each of the clamping members 13 and 17 are arranged in two substantially parallel rows so that the strands of tissue may be sutured in at least two spaced apart locations. Each row on clamping member 13 preferably extends from the proximal edge 32 to the distal edge 34 to include a proximal opening 51, a middle opening 52, and a distal opening 53. In a similar manner, each row on the clamping member 17 is provided with a proximal opening 56, a middle opening 57, and a distal opening 58. The parallel rows on each of the clamping members 13 and 17 are designed so that they are separated by a space wider than the respective arm to which each of the clamping members is attached. Such a separation is preferable as a needle may avoid any interference with arms 13 and 17 during suturing. It should be noted that although there are only two rows of openings 50 along each of the clamping members 13 and 17, if it is necessary, clamping members 13 and 17 may be designed to include additional rows along each of their widths.

When clamping members 13 and 17 are partially engaged to essentially form a continuous structure around a strands of tissue for suturing, each row of openings on one clamping member becomes aligned with a corresponding row of openings on the other clamping member to form a ring of openings around both clamping members (FIG. 4). For the ease of discussion, reference is now made only to one of the two rings of openings with the understanding that the components hereinafter disclosed for one ring of openings are similarly applicable to the other ring of openings. During the engagement between clamping members 13 and 17, each of the openings on clamping member 13 is substantially aligned with an opening on clamping member 17 so as to provide a path through which a needle may advance from one clamping member to the other. By way of example, distal opening 53 and proximal opening 51 on clamping member 13 are diagonally aligned with proximal opening 56 and distal opening 58 respectively on clamping member 17. While the distal and proximal openings on clamping members 13 and 17 are diagonally aligned, middle opening 52 on clamping member 13 and middle opening 57 on clamping member 17 are linearly aligned.

These correspondingly aligned openings on clamping members 13 and 17 may provide a path through which a needle is moved. However, as a needle advances from an one opening and through the strands of tissue, its course may be slightly altered so that realignment of the needle with an exiting opening may be needed. To improve the guidance of a needle from one clamping member to the other, looking again at FIG. 3, clamping members 13 and 17 may be provided with a thickness so that each opening 50 includes a tunnel 35. A tunnel, by the nature of its length, is better at providing guidance for an object to move therethrough than an opening. To this end, it is substantially easier to maneuver a needle, for example, across clamping member 13 and into a correspondingly aligned tunnel in clamping member 17. The alignment of tunnels 35 on and between clamping members 13 and 17 is preferably similar to the alignment of the openings on and between clamping member 13 and 17.

In FIG. 5, a plurality of slots 59 is shown positioned between certain adjacent openings 50 on clamping members 13 and 17. Slots 59, as is hereinafter explained, allow the suture thread to properly engage the strands of tissue. In particular, once a needle is advanced from, for example, distal opening 53 into an adjacent middle opening 52 of clamping member 13, slot 59 provides a passage through which the suture thread may avoid the clamping member when the thread is pulled across the adjacent openings and against the strands of tissue. Otherwise, the suture thread is forced to sit against clamping member 13 rather than against the strands of tissue. Each of the slots 59, as shown in FIG. 5, is preferably sized so that it is smaller in width than each of the openings 50 between which the slot is positioned. In this manner, only a suture thread with its smaller width relative to the width of a needle may move across slot 59. The needle, with its larger width, on the other hand, is prevented from doing the same.

In accordance with one embodiment of the present invention, there are four slots 59 in each ring of openings 50 when clamping members 13 and 17 are engaged. With reference to clamping member 13 in FIG. 4, there is a slot 59 between distal opening 53 and middle opening 52. Correspondingly, a slot 59 sits between distal opening 58 and middle opening 57 on clamping member 17. In addition, a slot 59 is provided between the distal opening 53 and distal opening 58 of clamping members 13 and 17 respectively. A slot 59 (not shown) also runs between proximal openings 51 and 56 across the respective proximal edge 32 and proximal edge 42 of clamping members 13 and 17. When clamping members 13 and 17 are disengaged from one another, as seen in FIG. 5, there now exist gaps 590 at the distal edge and the proximal edge of each of the clamping members 13 and 17 where slots 59 previously sit.

Suturing jig 10 is designed to securely hold strands of tissue that must subsequently be put into a patient. As such, arms 11 and 15, and clamping members 13 and 17 are preferably made from a rigid and strong, yet biocompatible material, for instance, stainless steel. Alternatively, arms 11 and 15, and clamping members 13 and 17 may be made from molded plastics.

In accordance with another embodiment of the present invention, arm 11, as can be seen in FIG. 1, may include at its proximal end 14 a loop 141, and arm 15 may include at its proximal end 18 a loop 181. Loops 141 and 181, being situated in a same plane, are configured for receiving a thumb and a finger of a surgeon. By providing each arm with a loop, arms 11 and 15 may be easily adjusted in a manner similar to a pair of scissors so as to vary a distance between clamping members 13 and 17. However, to ensure that clamping members 13 and 17 can sufficiently engage one another, loops 141 and 181 are each positioned to one side of its respective arm 11 and 15 so that the arms 11 and 15 may be sit flush against one another.

On occasion, it may be desirable to maintain a tight and close engagement between clamping members 13 and 17 without having to continually apply a force to the arms 11 and 15. Accordingly, in one embodiment of the invention, arms 11 and 15 are respectively provided with mutually engaging locking mechanisms 190 and 192. Each of the locking mechanisms 190 and 192, being positioned within the same plane as the loops 141 and 181, includes a plurality of teeth 194 along its engaging surface. The teeth 194 are oriented so that they angle in one direction on locking mechanism 190 and in an opposite direction on locking mechanism 192. In this manner, the teeth 194 on each of the locking mechanisms 190 and 192 may move past one another to securely maintain an engagement between the first and second clamping members 13 and 17.

Figure 6:
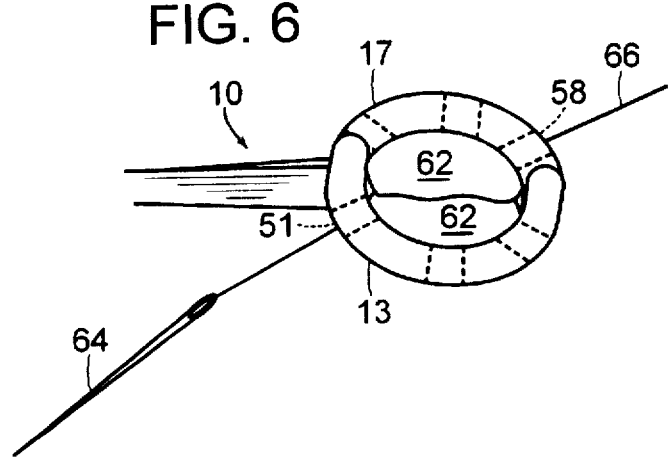
FIGS. 6–9 show, in series, the steps for suturing strands of tissue using the suturing jig shown in FIG. 1 in accordance with one embodiment of the present invention.
Figure 7:
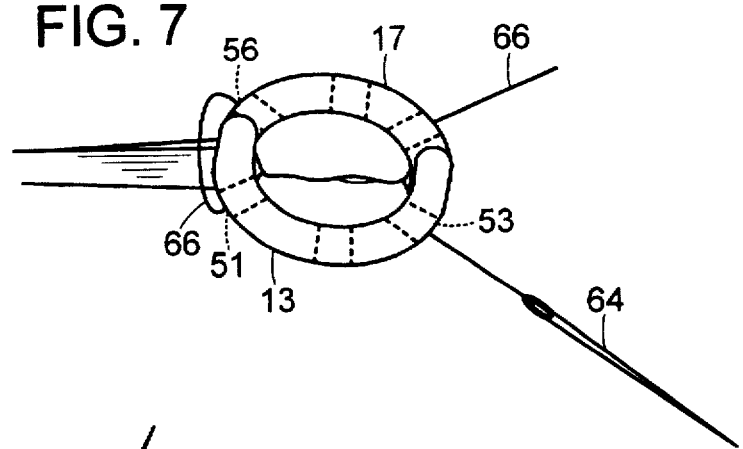
Figure 8:
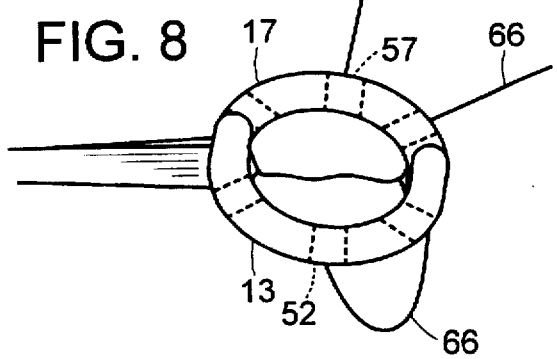
Figure 9:
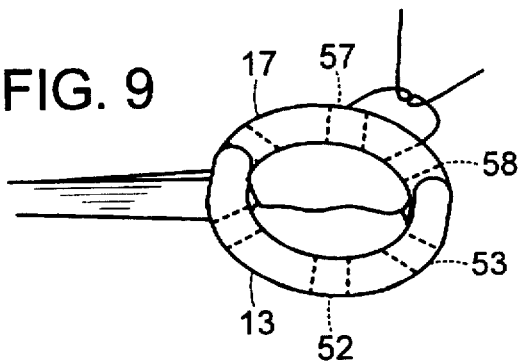

FIGS. 6 through 9 illustrate one method of the present invention for which the suturing jig 10 may be used for the suturing of multiple strands of tissue for use as ligament replacement. Initially, the strands of tissue 62 are positioned on clamping member 13. Thereafter, arms 11 and 15 are pivotally adjusted to move clamping members 13 and 17 toward one another until they form a substantially continuous structure to secure the strands of tissue 62 therein. As shown in FIG. 6, a needle 64 with an attached suture thread 66 is next inserted through the distal opening 58 on clamping member 17, pushed diagonally across the strands of tissue 62, and pulled out through the proximal opening 51 on clamping member 13. After needle 64 is pulled from the proximal opening 51 on clamping member 13, a lengthy end to suture thread 66 is left extending from distal opening 58 on clamping member 17. Needle 64 is then inserted through the proximal opening 56 on clamping member 17, and pushed diagonally across the strands of tissue 62. As needle 64 is pulled from distal opening 53, FIG. 7, suture thread 66 moves across slot 59 between proximal opening 51 on clamping member 13 and proximal opening 56 on clamping member 17 to engage the strands of tissue 62. The suturing process may further proceed by subsequently inserting the needle 64 through the middle opening 52 on clamping member 13, across the strands of tissue 62, and out through middle opening 57 on clamping member 17, FIG. 8. Once needle 64 is pulled from middle opening 57 along with suture thread 66, suture thread 66 is removed from needle 64. The suture thread end from middle opening 57 and the suture thread end from distal opening 58 are thereafter pulled to advance suture thread 66 across slot 59 between middle opening 52 and distal opening 53 on clamping member 13. After the suturing process is completed and the needle is disconnected from the suture thread, a knot may be formed between the suture thread ends and tightened across slot 59 between middle openings 57 and distal opening 58 on clamping member 17, FIG. 9. The suturing process may be repeated along the next row of openings 50 on clamping members 13 and 17 as previously described to ensure that the strands of tissue are tightly attached. If suturing is necessary beyond the number of rows provided along each of the clamping members 13 and 17, suture jig 10 may be moved to an adjacent area on the strands of tissue 62 and the suturing process repeated.

Although the suturing jig 10 of the present invention is preferably used for attaching strands of tissue for use as a ligament replacement, jig 10 may also be used, for example, to attach a ligament replacement to a bone block. To perform such a procedure, simply secure the bone block and replacement ligament between the clamping members 13 and 17 and maneuver needle 64 with a suture thread 66 in the manner described above.

While the invention has been described in connection with specific embodiments thereof, it will be understood that it is capable of further modification. This application is intended to cover any variations, uses, or adaptations of the invention and including such departures from the present disclosure as come within known or customary practice in the art to which the invention pertains.

What is claimed is:

1. A surgical jig for use in suturing tissue, the jig comprising:
    a first member having a first arcuate distal end;
    a second member having a second arcuate distal end and being pivotally attached to the first member, such that the first and second arcuate distal ends are bent toward one another;
    a plurality of openings at each of the first and second distal ends for guiding a needle and suture thread through the first and second distal ends; and
    a plurality of slots, each being located between adjacent openings to allow a portion of the suture thread to move between the adjacent openings.

2. A surgical jig for use in suturing tissue, the jig comprising:
    a pair of opposing clamping members bent toward one another for circumferentially engaging the tissue;
    a first arm being attached at its distal end to one clamping member, and a second arm being attached at its distal end to the opposing clamping member, the first and second arms being pivotably connected to one another for variably adjusting a distance between the respective clamping members;
    a plurality of openings positioned on each clamping member for guiding a needle and suture thread from one clamping member to the other; and
    a plurality of slots, each slot being positioned between adjacent openings for allowing a portion of the suture thread to move between the adjacent openings.

3. A jig as set forth in claim 2, wherein the clamping members are sized to engage one another.

4. A jig as set forth in claim 3, wherein each of the clamping members is arcuate in shape.

5. A jig as set forth in claim 2, wherein the openings on each clamping member are in alignment relative to one another so as to include a proximal opening, a middle opening and a distal opening.

6. A jig as set forth in claim 5, wherein each opening on a clamping member is in alignment with a corresponding opening on the other clamping member.

7. A jig as set forth in claim 6, wherein the distal opening on one clamping member is diagonally aligned with the proximal opening on the other clamping member, and the middle opening on one clamping member is axially aligned with the middle opening on the other clamping member.

8. A jig as set forth in claim 2, wherein each slot is smaller in width than each opening so as to prevent the needle from moving into the slot.

9. A jig as set forth in claim 2 further including a locking mechanism for securely maintaining an engagement between the clamping members.

10. A jig as set forth in claim 2, wherein the openings on each clamping member are arranged in parallel rows, each row including a proximal opening, a middle opening, and a distal opening.

11. A jig as set forth in claim 2, wherein each of the openings includes a tunnel.

12. A surgical jig for use in suturing tissue, the jig comprising:

a pair of opposing clamping members;

a first arm being attached at its distal end to one clamping member, and a second arm being attached at its distal end to the opposing clamping member, the first and second arms being pivotally connected to one another for variably adjusting a distance between the respective clamping members;

a plurality of openings positioned on each clamping member for guiding a needle and suture thread from one clamping member to the other, the openings on each clamping members being in alignment relative to one another, so as to include a proximal opening, a middle opening and a distal opening and being in alignment with a corresponding opening on the other clamping member, such that the distal opening on one clamping member is diagonally aligned with the proximal opening on the other clamping member, and the middle opening on one clamping member is axially aligned with the middle opening on the other clamping member; and a plurality of slots, each slot being positioned between adjacent openings for allowing a portion of the suture thread to move between the adjacent openings.

13. A surgical jig for use in suturing tissue, the jig comprising:

a pair of opposing clamping members;

a first arm being attached at its distal end to one clamping member, and a second arm being attached at its distal end to the opposing clamping member, the first and second arms being pivotally connected to one another for variably adjusting a distance between the respective clamping members;

a plurality of openings positioned on each clamping member for guiding a needle and suture thread from one clamping member to the other, the openings on each clamping member being arranged in parallel rows, each row including a proximal opening, a middle opening and a distal opening; and a plurality of slots, each slot being positioned between adjacent openings for allowing a portion of the suture thread to move between the adjacent openings.

14. A surgical jig for use in suturing tissue, the jig comprising:

a pair of opposing clamping members;

a first arm being attached at its distal end to one clamping member, and a second arm being attached at its distal end to the opposing clamping member, the first and second arms being pivotally connected to one another for variably adjusting a distance between the respective clamping members;

a plurality of openings positioned on each clamping member for guiding a needle and suture thread from one clamping member to the other, each of the openings including a tunnel; and a plurality of slots, each slot being positioned between adjacent openings for allowing a portion of the suture thread to move between the adjacent openings.

15. A surgical jig for use in suturing strands of tissue, the jig comprising:

first and second arms being pivotally attached to one another, each arm having a distal end and a proximal end;

a pair of opposing clamping members, each member extending from the distal end of each arm and bent toward the other in a manner which permits the members to circumferentially engage the strands of tissue;

a pair of loops, each loop being situated at the proximal end of each arm for pivotally moving the arms so as to variably adjust a distance between the respective clamping members;

a plurality of openings positioned on each clamping member, the openings being adapted to guide a needle and suture thread from one clamping member to the other clamping member; and a plurality of slots, each slot being positioned between adjacent openings for allowing a portion of the suture thread to move between the adjacent openings.

16. A jig as set forth in claim 15, wherein one clamping member is sized to partially receive the other clamping member.

17. A jig as set forth in claim 16, wherein each of the clamping members is arcuate in shape.

18. A jig as set forth in claim 15, wherein each slot is smaller in width than each opening so as to prevent the needle from moving into the slot.

19. A jig as set forth in claim 15, further including a locking mechanism for securely maintaining an engagement between the clamping members.

20. A jig as set forth in claim 15, wherein the openings on each of the clamping members are arranged in parallel rows, each row including a proximal opening, a middle opening, and a distal opening.

21. A jig as set forth in claim 20, wherein each row of openings on one clamping member is in alignment with a corresponding row of openings on the other clamping member.

22. A jig as set forth in claim 21, wherein between two correspondingly aligned rows the distal opening on one clamping member is diagonally aligned with the proximal opening on the other clamping member, and the middle opening on one clamping member is axially aligned with the middle opening on the other clamping member.

23. A jig as set forth in claim 15, wherein each of the openings includes a tunnel.

24. A surgical jig for use in suturing strands of tissue, the jig comprising:

first and second arms being pivotally attached to one another, each arm having a distal end and a proximal end;

a pair of opposing clamping members, each member extending from the distal end of each arm;

a pair of loops, each loop being situated at the proximal end of each arm for pivotally moving the arms so as to variably adjust a distance between the respective clamping members;

a plurality of openings positioned on each clamping member, the openings being adapted to guide a needle and suture thread from one clamping member to the other clamping member, the openings on each of the clamping members being arranged in parallel rows, each row including a proximal opening, a middle opening and a distal opening; and a plurality of slots, each slot being positioned between adjacent openings for allowing a portion of the suture thread to move between the adjacent openings.

25. A jig as set forth in claim 24, wherein each row of openings on one clamping member is in alignment with a corresponding row of openings on the other clamping member.

26. A jig as set forth in claim 25, wherein between two correspondingly aligned rows the distal opening on one clamping member is diagonally aligned with the proximal opening on the other clamping member, and the middle opening on one clamping member is axially aligned with the middle opening on the other clamping member.

27. A surgical jig for use in suturing strands of tissue, the jig comprising:

first and second arms being pivotally attached to one another, each arm having a distal end and a proximal end;

a pair of opposing clamping members, each member extending from the distal end of each arm;

a pair of loops, each loop being situated at the proximal end of each arm for pivotally moving the arms so as to variably adjust a distance between the respective clamping members;

a plurality of openings positioned on each clamping member, the openings being adapted to guide a needle and suture thread from one clamping member to the other clamping member, each of the openings including a tunnel; and a plurality of slots, each slot being positioned between adjacent openings for allowing a portion of the suture thread to move between the adjacent openings.

28. A method for suturing strands of tissue comprising the steps of:

(a) providing a suturing jig having a pair of arms pivotally attached to one another, a pair of opposing clamping members, each member extending from a distal end of each arm, a plurality of openings on each clamping member, and a plurality of slots, each slot being positioned between adjacent openings;

(b) pivotally adjusting the arms so as to secure strands of tissue between the clamping members;

(c) maneuvering a needle having a suture thread attached thereto through a first opening on one clamping member, across the strands of tissue, and out through a corresponding second opening on an opposing clamping member;

(d) inserting the needle through a third opening adjacent the second opening, across the strands of tissue, and out through a corresponding fourth opening; and (e) pulling the suture thread across the slot between the adjacent second and third openings against the strands of tissue.

29. A method as set forth in claim 28 further comprising:

(f) tying each end of the suture thread to one another so as to form a knot across the slot between the first and fourth openings.

30. A method for suturing strands of tissue comprising the steps of:

(a) providing a suturing jig comprising a pair of arms pivotally attached to one another, a pair of clamping members, each member extending from a distal end of each arm, a plurality of aligned openings on each clamping member, and a plurality of slots, each slot being positioned between adjacent openings;

(b) pivotally adjusting the first and second arms toward one another until strands of tissue are secured between the clamping members;

(c) inserting needle having a suture thread attached thereto through a first opening on one clamping member, across the strands of tissue, and out through a diagonally aligned second opening on an opposing clamping member;

(d) pulling the needle from the second opening so as to pull the suture thread through the strands of tissue while leaving a first end portion of the thread extending form the first opening;

(e) inserting the needle through a third opening on the one clamping member, across the strands of tissue, and out through a diagonally aligned fourth opening on the opposing clamping member; and (f) pulling the needle from the fourth opening so as to pull the suture thread across the slot between the third opening on the one clamping member and the second opening on the opposing clamping member.

31. A method as set forth in claim 30 further comprising the steps of:

(g) inserting the needle through a fifth opening on the opposing clamping member, across the strands of tissue, and out through a sixth opening on the one clamping member; and (h) pulling the needle from the sixth opening so as to pull the suture thread across the slot between the fourth and fifth openings on the opposing clamping member.

32. A method as set forth in claim 31 further comprising:

disconnecting the needle from the suture thread so as to leave a second end portion of the thread extending from the sixth opening; and tying each end portion of the suture thread to one another so as to form a knot across the slot between the sixth and first opening on the one clamping member.

33. A method as set forth in claim 30 further comprising:

disconnecting the needle from the suture thread so as to leave a second end portion of the thread extending from the fourth opening; and tying each end portion of the suture thread to one another so as to form a knot across the slot between the fourth on the opposing clamping member and first opening on the one clamping member.

34. A jig for use in suturing tissue, the jig comprising:

a first member having a first arcuate distal end which defines a recess having a recess plane and a first recess axis that is substantially transverse to the recess plane;

a second member having a second arcuate distal end which defines a recess having a recess plane and a second recess axis that is substantially transverse to the recess plane, the second member being pivotally attached to the first member such that the first and second members pivot in a plane that is substantially transverse to the first and second recess axes;

a plurality of openings at each of the first and second distal ends for guiding a needle and suture thread through the first and second distal ends; and a plurality of slots, each being located between adjacent openings to allow a portion of the suture thread to move between the adjacent openings.

35. A jig for use in suturing tissue, the jig comprising:

a first member terminating in a first arcuate distal end having an inside surface and an opposing outside surface;

a second member terminating in a second arcuate distal end having an inside surface and an opposing outside surface, the second member being pivotally attached to the first member such that the inside surfaces of the first and second arcuate distal ends face one another;

a plurality of openings at each of the first and second distal ends for guiding a needle and suture thread through the first and second distal ends, each opening extending from the outside surface to the inside surface;

a plurality of slots, each being located between adjacent openings to allow a portion of the suture thread to move between the adjacent openings.

36. A jig for use in suturing tissue, the jig comprising:

a first member terminating in a first arcuate distal end having an inside surface and an opposing outside surface;

a second member terminating in a second arcuate distal end having an inside surface and an opposing outside surface, the second member being pivotally attached to the first member;

a plurality of openings at each of the first and second distal ends for guiding a needle and suture thread through the first and second distal ends, each opening extending from the outside surface to the inside surface substantially in a direction in which the first and second members pivot;

a plurality of slots, each being located between adjacent openings to allow a portion of the suture thread to move between the adjacent openings.

* * * * *